US012616447B2

(12) United States Patent
Novell et al.

(10) Patent No.: US 12,616,447 B2
(45) Date of Patent: May 5, 2026

(54) METHOD AND SYSTEM FOR SPECTRAL ANALYSIS AND DETERMINATION OF A MARKER MAKING IT POSSIBLE TO ENSURE THE SAFETY OF THERAPEUTIC ULTRASOUND INTERVENTIONS

(71) Applicant: COMMISSARIAT A L'ENERGIE ATOMIQUE ET AUX ENERGIES ALTERNATIVES, Paris (FR)

(72) Inventors: Anthony Novell, Orsay (FR); Hermes Salles Kamimura, New York, NY (US); Benoît Larrat, Paris (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 335 days.

(21) Appl. No.: 17/281,195

(22) PCT Filed: Oct. 16, 2019

(86) PCT No.: PCT/EP2019/078098
§ 371 (c)(1),
(2) Date: Mar. 29, 2021

(87) PCT Pub. No.: WO2020/083725
PCT Pub. Date: Apr. 30, 2020

(65) Prior Publication Data
US 2021/0393239 A1 Dec. 23, 2021

(30) Foreign Application Priority Data
Oct. 24, 2018 (FR) .......................................... 1859826

(51) Int. Cl.
*A61B 8/00* (2006.01)
*A61B 8/08* (2006.01)
*G01N 29/34* (2006.01)

(52) U.S. Cl.
CPC ................ *A61B 8/481* (2013.01); *A61B 8/52* (2013.01); *G01N 29/348* (2013.01); *A61B 8/0808* (2013.01)

(58) Field of Classification Search
CPC ......... A61B 8/481; A61B 8/52; A61B 8/0808; A61B 8/4488; G01N 29/348;
(Continued)

(56) References Cited

U.S. PATENT DOCUMENTS

| 2010/0056924 | A1 | 3/2010 | Powers | |
|---|---|---|---|---|
| 2012/0130288 | A1* | 5/2012 | Holland | ................... A61B 8/06 601/2 |

(Continued)

FOREIGN PATENT DOCUMENTS

| JP | 5-76539 A | 3/1993 |
|---|---|---|
| JP | 2003-33365 A | 2/2003 |

(Continued)

OTHER PUBLICATIONS

McDannold, et al., "Targeted disruption of the blood-brain barrier with focused ultrasound: association with cavitation activity", Phys Med Biol., vol. 51, No. 4, pp. 793-807, Feb. 21, 2006.
(Continued)

*Primary Examiner* — Christopher Koharski
*Assistant Examiner* — Aminah Asghar
(74) *Attorney, Agent, or Firm* — Baker Hostetler

(57) ABSTRACT
A method for performing spectral analysis and determining a safety marker includes an assembly via which: regularly, during shot Bb, at a series of times ta, the variation as a function of time in the spectral lines corresponding to the subharmonic and ultra-harmonic frequencies of a received acoustic-response signal of the microbubbles is measured, and the variation as a function of time, over the times ta, in a safety marker is determined and quantified, the safety
(Continued)

marker being defined, at each time ta, by a number MDDa equal to the ratio of the sum of the areas of the spectral lines, measured at the time ta and corresponding to the subharmonic and/or ultra-harmonic frequencies of the received acoustic-response signal of the microbubbles, to the sum of the areas of the spectral lines, measured at the first time t1 and corresponding to the subharmonic and/or ultra-harmonic frequencies of the acoustic-response signal of the microbubbles. A system for performing spectral analysis and determining a safety marker implements said method.

12 Claims, 6 Drawing Sheets

(58) Field of Classification Search
CPC ... A61N 2007/0039; A61N 2007/0086; A61M 37/0092
See application file for complete search history.

(56) References Cited

U.S. PATENT DOCUMENTS

| | | | |
|---|---|---|---|
| 2012/0271169 A1* | 10/2012 | Coussios | A61N 7/02 |
| | | | 600/439 |
| 2013/0006106 A1 | 1/2013 | O'Reilly et al. | |
| 2016/0066799 A1* | 3/2016 | Berkow | A61B 5/02116 |
| | | | 600/479 |
| 2016/0144203 A1* | 5/2016 | Holland | A61N 7/00 |
| | | | 601/2 |
| 2019/0350557 A1* | 11/2019 | Shi | A61B 8/0891 |
| 2020/0015876 A1* | 1/2020 | Chou | A61B 18/00 |

FOREIGN PATENT DOCUMENTS

| | | | |
|---|---|---|---|
| JP | 2016-221302 A | 12/2016 | |
| WO | 2008/062342 A1 | 5/2008 | |
| WO | 2012/042423 A1 | 4/2012 | |

OTHER PUBLICATIONS

Kamimura, et al., "Feedback control of microbubble cavitation for ultrasound-mediated blood-brain barrier disruption in non-human primates under magnetic resonance guidance", J Cereb Blood Flow Metab., vol. 39, No. 7, pp. 1191-1203, Jul. 2019.

Coussios, et al., "Role of acoustic cavitation in the delivery and monitoring of cancer treatment by high-intensity focused ultrasound (HIFU)", Int. J. Hyperthermia, 23 (2), pp. 105-120, Mar. 2007.

Konofagou, et al., "Ultrasound-Induced Blood-Brain Barrier Opening", Curr. Pharma. Biotechnol., 13(7), pp. 1332-1345, 2012.

Shekhar, et al., "The delayed onset of subharmonic and ultraharmonic emissions from a phospholipid-shelled microbubble contrast agent", Ultrasound in Med. & Biol., 40(4), pp. 727-738, 2014.

O'Brien, et al., "Surfactant shedding and gas diffusion during pulsed ultrasound through a microbubble contrast agent suspension", J. Acoust. Soc. Am., 134, No. 2, pp. 1416-1427, 2013.

Kooiman, et al., "Focal areas of increased lipid concentration on the coating of microbubbles during short tone-burst ultrasound insonification", PLoS One 12 (7): e0180747, 2017.

Haqshenas, et al., "Multi-resolution analysis of passive cavitation detector signals", Journal of Physics, 13th Anglo-French Physical Acoustics Conference (AFPAC2014), 2015.

O'Reilly, et al., "Blood-Brain Barrier: Real-time Feedback-controlled Focused Ultrasound Disruption by Using an Acoustic Emissions-based Controller", Radiology, 263(1), pp. 96-106, 2012.

Tsai, et al., "Real-time monitoring of focused ultrasound bloodbrain barrier opening via subharmonic acoustic emission detection: implementation of confocal dual-frequency piezoelectric transducers", Phys. Med. Biol., 61, pp. 2926-2946, 2016.

English translation of Notice of Rejection issued in Japanese Patent Application No. 2021-522487 dated Jul. 18, 2023.

* cited by examiner

102

METHOD AND SYSTEM FOR SPECTRAL ANALYSIS AND DETERMINATION OF A MARKER MAKING IT POSSIBLE TO ENSURE THE SAFETY OF THERAPEUTIC ULTRASOUND INTERVENTIONS

CROSS-REFERENCE TO RELATED APPLICATIONS

This application is a National Stage of International patent application PCT/EP2019/078098, filed on Oct. 16, 2019, which claims priority to foreign French patent application No. FR 1859826, filed on Oct. 24, 2018, the disclosures of which are incorporated by reference in their entirety.

FIELD OF THE INVENTION

The present invention relates to a method for performing spectral analysis of the acoustic response of a biological tissue and for determining a safety marker allowing the safety of therapeutic ultrasound interventions to be ensured.

The invention also relates to a corresponding system for performing spectral analysis of the acoustic response of a biological tissue and for determining a safety marker allowing the safety of therapeutic ultrasound interventions to be ensured.

BACKGROUND

The biological tissue is any soft vascularized biological tissue, for example a tissue comprised in the set of the tissues of the brain, liver, heart, muscles, breasts, kidneys, eyes, thyroid, prostate, uterus, tendons, pancreas, and skin, and preferably a brain tissue.

Despite the increase in the number of active drugs and the emergence of targeted therapies in oncology, the therapeutic progress that has been made with respect to brain diseases (cancer included) still remains modest. One of the major obstacles resides in the inability to deliver therapeutic molecules to the tissues in a specific and controlled manner. Specifically, the walls of the blood vessels of the brain form a very effective endothelial barrier called the blood-brain barrier. This barrier limits the passage of molecules from the blood to the cells to be treated. Current methods for administering therapeutic agents are invasive, non-localized, or pose a high risk to the patient. Furthermore, the free circulation of therapeutic substances through the organism has undesirable effects on healthy tissues. Efficient, specific and localized delivery of therapeutic molecules is therefore a major challenge. Since 2000, many studies have demonstrated that focused ultrasound may be used to accomplish this task. Combined with the intravenous injection of gas microbubbles, ultrasound may be used to induce localized and reversible opening of biological barriers. Specifically, the mechanical forces (i.e., micro-flows and oscillations) resulting from the bubble-ultrasound interactions (cavitation) weaken the barrier and promote the passage of molecules into the brain tissue in general, and in particular into the diseased region that it is sought to treat if the latter is correctly targeted by the ultrasound beam. The treatment possibly lasting several hours, how effectively the barrier is kept open in terms of passage of large molecules and the safety of the technique may be controlled by modifying ultrasonic parameters.

The delivered "cavitation dose" plays a major role in the effectiveness and safety of this technology. The acoustic pressure within the treated tissue must be sufficient to cause a controlled oscillation of the microbubbles (stable cavitation regime) and to generate a reversible and non-lesional permeabilization of the vascular walls.

In contrast, subjected to excessively high acoustic pressures, the microbubbles then enter into an inertial cavitation regime involving locally violent physical effects (i.e. shock waves, micro-jets, local implosion of the bubble) that may lead to deterioration of tissues and to the onset of serious side effects (e.g., inflammation, hemorrhaging).

The difference between an effective dose and a lesional dose is small and hence new precise in situ dosimetry methods need to be developed. As this technology is about to start clinical trials, it would be highly desirable to be able to control cavitation dose in real time.

In the context of opening of the blood-brain barrier by ultrasound, the objective is to keep a high degree of stable cavitation (effectiveness) during the treatment while keeping inertial cavitation at a low level (safety). In trans-skull ultrasound therapy, the non-uniformity of the skull may have an undesirable influence on the effectiveness and safety of the technique.

Specifically, since the thickness of the skull varies depending on the region, the attenuation of the ultrasound beam is correspondingly modified. The amplitude of the ultrasonic wave may easily vary by a factor of 2 from one point to another in humans. For large animals and more particularly non-human primates, the presence of tissues (e.g. muscles) between the skin and the skull may also affect the ultrasound beam.

Thus, when the ultrasound is transmitted through a region that is thicker than expected, the amplitude of the ultrasonic wave in the region of interest will be lower and the treatment potentially ineffective (i.e., the acoustic pressure will be insufficient to allow a noticeable oscillation of the microbubbles to be achieved).

In contrast, if the region is thinner, the amplitude of the ultrasonic wave will be underestimated and safety problems resulting from the inertial cavitation of the bubbles may arise.

Cavitation may be detected passively using ultrasonic transducers placed around the treated region. These sensors allow the frequency response of the microbubbles to be measured and thus the induced cavitation regime to be determined in real time, as described in the article by Coussios et al., titled "Role of acoustic cavitation in the delivery and monitoring of cancer treatment by high-intensity focused ultrasound (HIFU)" and published in Int. J. Hyperthermia, March 2007, 23 (2), pp. 105-120.

One current challenge is how to discriminate between the response of the microbubbles and that of surrounding tissues, and then to ensure that this response corresponds to stable cavitation. Conventionally, the stable component of the cavitation dose is determined via the harmonic signal of the microbubbles: $(n+1) f_0$ (with $n \in \mathbb{N}^*$ and $f_0$ the emission frequency of the ultrasound) whereas the inertial component of the cavitation dose corresponds to the measurement of the signal emitted at all frequencies (wide-band signal), as described in the article by Konofagou et al. (2012), titled "Ultrasound-Induced Blood-Brain Barrier Opening" and published in Curr. Pharma. Biotechnol.; 13(7), pp. 1332-1345.

However, these cavitation markers lack robustness and sensitivity. Undesirable events (e.g., edema) may occur despite the precautions taken. There is therefore a need for other more reliable and reproducible indicators.

As is known, the microbubbles are generally composed of a heavy gas (perfluorocarbon, sulfur hexafluoride) in order to decrease their rate of dissolution in the blood and thus to increase the length of the echographic examination, which may reach several minutes. This gas is surrounded by a shell the function of which is to protect the bubble. The thickness of the wall varies from a few nm to several hundred nm. It is generally composed of proteins, phospholipids, surfactants or polymers.

Recent in vitro work, as described in the article by Shekar et al. (2014), titled "The delayed onset of subharmonic and ultraharmonic emissions from a phospholipid contrast agent" and published in Ultrasound in Med. & Biol., 40(4), pp. 727-738, have demonstrated the appearance of specific oscillations of the microbubbles when the latter are subjected to particular conditions. Specifically, over time the gas contained in the bubble diffuses into the surrounding medium, causing its envelope to buckle (e.g. excess lipid on the envelope of the bubble). This state is associated with the appearance of specific frequencies (namely sub-harmonic and ultra-harmonic frequencies:

$$\frac{(2n+1)}{2}$$

with $n \in \mathbb{N}$ and $f_0$ the emission frequency of the ultrasound) and may lead to the disappearance of the microbubble.

This effect is accentuated by the application of long ultrasonic sequences that promote the diffusion of the gas, as described in the article by O'Brien et al. (2013), titled "Surfactant shedding and gas diffusion during pulsed ultrasound through a microbubble contrast agent suspension" and published in J. Acoust. Soc. Am., 134, 1416-27, and the buckling of the envelope of the microbubble, as described in the article by Kooiman et al. (2017), titled "Focal areas of increased lipid concentration on the coating of microbubbles during short tone-burst ultrasound insonification" and published in PLoS ONE 12 (7): e0180747.

This state of destabilization of the microbubbles appears during ultrasonic excitation and has not to date been used as a marker of the risk of undesirable effects during ultrasound therapy assisted by gas microbubbles.

It would therefore seem that it is in fact possible to define three regimes of microbubble activity: stable cavitation (harmonic radiation only), inertial cavitation (harmonic, sub-harmonic, ultra-harmonic and wide-band radiation) and an intermediate regime corresponding to a destabilization of the shell of the microbubbles (harmonic, sub-harmonic and ultra-harmonic radiation).

The work being carried out at the present time with regard to measuring cavitation activity is mainly focused on the harmonic components and the wide-band spectrum.

Currently, a consensus has not been reached by the scientific community as to using sub/ultra-harmonic components as a marker of stable activity or inertial cavitation, as attested by the article by Haqshenas et al. (2015), titled "Multi-resolution analysis of passive cavitation detector signals", and published in the Journal of Physics, doi: 10.1088/1742-6596/581/1/012004.

In order to avoid the detrimental effects associated with the use of an excessively high acoustic pressure, in current work a "tolerable" cavitation threshold is determined based on the exploitation of the wide-band signal or on analysis of one or more specific frequency components (e.g., harmonics, sub-harmonics, ultra-harmonics). Among this current work, mention may be made of that described in the following documents:

the article by O'Reilly et al. (2012), titled "Blood-Brain Barrier: Real-time Feedback-controlled Focused Ultrasound Disruption by Using an Acoustic Emissions-based Controller", and published in Radiology, 263(1), pp. 96-106;

the article by Tsai et al. (2016), titled "Real-time monitoring of focused ultrasound bloodbrain barrier opening via subharmonic acoustic emission detection: implementation of confocal dual-frequency piezoelectric transducers", and published in Phys. Med. Biol., 61, pp. 2926-2946;

the article by Kamimura et al. (2018), titled "Feedback control of microbubble cavitation for ultrasound-mediated blood-brain barrier disruption in non human primates under magnetic resonance guidance", and published in J. Cereb. Blood Flow Metab. 1:271678X17753514;

patent application WO2012042423 A1; and patent application WO2008062342 A3.

Whether information is processed in real time or not, whether feedback is provided on the current ultrasonic shot or not, and whether an absolute or relative radiation spectrum is measured, in all this current work cavitation doses are computed shot after shot, one value for each shot. These safety markers lack sensitivity and in some cases do not prevent the appearance of detrimental effects.

The technical problem is to provide a more sensitive, more robust and more reliable safety marker that allows the appearance of detrimental effects on a tissue subjected to an exposure to therapeutic ultrasound to be avoided, and to provide a method allowing this therapeutic marker to be determined.

SUMMARY OF THE INVENTION

To this end, one subject of the invention is a method for performing spectral analysis and determining a safety marker that is representative of a state of destabilization of microbubbles contained in a region of a soft vascularized biological tissue, said microbubbles being subjected to an ultrasonic excitation signal at a predetermined emission frequency $f_0$ in order to induce localized and reversible opening of the biological barriers in said region, and said state of destabilization of the microbubbles being detrimental to the biological tissue, and said ultrasonic excitation signal being formed by an ultrasonic sequence composed of a predetermined integer number Nb, higher than or equal to 1, of wave trains, called "shots". The method for detecting and determining a safety marker is characterized in that, after each shot Bb has been triggered, b being comprised between 1 and Nb, a system for performing spectral analysis and determining a safety marker:

regularly measures, during the shot Bb, at a series of times ta, the variation as a function of time in the spectral lines corresponding to the subharmonic and ultra-harmonic frequencies of the received acoustic-response signal of the microbubbles, the received response signal being detected by a passive cavitation detector having a predetermined detection passband, and determines, by quantifying it, the variation as a function of time, over the times ta, in a safety marker that is defined, at each time ta, by a number $MDD_a$ equal to the ratio of the sum of the areas of the spectral lines, measured at the time ta and corresponding to the subharmonic and/or ultra-harmonic frequencies of the received acoustic-response signal of the microbubbles, to the sum of the areas of the spectral lines, measured at the first time t1 and corresponding to the subharmonic and/or ultra-harmonic frequencies of the acoustic-response signal of the microbubbles in their initial state.

According to particular embodiments, the method for performing spectral analysis and determining a safety marker comprises one or more of the following features:

the measurement, at each time ta, of the spectral lines corresponding to the subharmonic and/or ultra-harmonic frequencies of the received acoustic-response signal of the microbubbles exploits the response signal received in an observation window wa that contains the time ta and that is included in the reception time interval corresponding to the shot in question;

the observation or analysis windows wa are adjacent or separate or partially overlap pairwise;

the method for performing spectral analysis and determining a safety marker described above comprises, for a given shot Bb, b being comprised between 1 and Nb, a first measuring and segmenting step in which the acoustic-response signal of the microbubbles to the wave train Bb is broken up into a predetermined integer number k, k being higher than or equal to 2, of time windows wa, a varying from 1 to k, of equal durations that allow the variation in the frequency components during the ultrasonic wave train Bb to be determined, said signal being received and measured by the passive cavitation detector;

the number k of windows and their sizes tw depend directly on the duration and on the excitation frequency $f_0$ of the ultrasonic shot Bb, the duration of the ultrasonic shot being comprised between a few microseconds and several hundred milliseconds;

the duration of the windows wa is comprised between the duration of 8 cycles of the excitation signal and half the duration of one shot, and/or the number k of windows wa is higher than or equal to 2 and lower than or equal to one eighth of the product of the duration of one shot $T_B$ multiplied by the ultrasonic excitation frequency $f_0$;

the method for performing spectral analysis and determining a safety marker described above comprises, for a given shot Bb, b being comprised between 1 and Nb, a spectra-computing second step, which is executed after the first step, and in which, for each window wa of the shot Bb, a varying from 1 to k, the system for performing spectral analysis and determining a safety marker computes the frequency spectrum of the portion, of the acoustic-response signal of the microbubbles to the wave train Bb, that is contained in said window wa;

the method for computing the frequency spectra uses a Fourier transform;

the method for performing spectral analysis and determining a safety marker, defined above, comprises, for a given shot Bb, b being comprised between 1 and Nb, a third step of computing the variation, during the shot, in a cavitation signal s(a), which step is executed after the second step, and in which, for each time window we, a varying from 1 to k, the system for performing spectral analysis and determining a safety marker computes the cavitation signal s(a) to be the sum of the areas of the spectral lines measured at the time ta and corresponding to the subharmonic and/or ultra-harmonic frequencies of the acoustic-response signal of the microbubbles;

the number of ultra-harmonic and/or subharmonic components considered in the computation of the cavitation signal s(a) depends on the passband of the one or more transducers used to detect the cavitation and that form the passive cavitation detector;

the amplitude of the measured peaks of the ultra-harmonic and/or subharmonic components comprised in the passband of the passive cavitation detector are used in addition to or instead of the cavitation signal s(a) in the computation;

the method for performing spectral analysis and determining a safety marker, described above, comprises, for a given shot Bb, b being comprised between 1 and Nb, a fourth step of computing the variation, during the shot, in a cavitation marker s(a), which step is executed after the third step (108), and in which, for each time window wa of the shot Bb, a varying from 1 to k, the system for performing spectral analysis and determining a safety marker computes a safety marker called the "cavitation dose $MDD_a$", this safety marker being defined by a number $MDD_a$ equal to the ratio of the cavitation signal s(a) in the a-th window wa to the cavitation signal s(1) of the first time window w1, the cavitation dose $MDD_a$ being expressed on a linear or logarithmic scale;

the method for performing spectral analysis and determining a safety marker, described above, comprises, for a given shot Bb, b being comprised between 1 and Nb, a fifth step of computing the variation, during the shot, in a first warning parameter Al1(a) and/or in a second warning parameter Al2(a), which step is executed after the fourth step, and in which the first warning parameter Al1 is put in an active state when the safety marker $MDD_a$ exceeds a first predetermined safety threshold value Th1, and the second warning parameter Al2 is put in an active state when the number of times nf the safety marker $MDD_a$ has exceeded the first threshold value Th1 has exceeded a second predetermined threshold value Th2;

the method for performing spectral analysis and determining a safety marker, described above, comprises, for a given shot Bb, b being comprised between 1 and Nb, a sixth step, which step is executed after the fourth or the fifth step, and in which the system for performing spectral analysis and determining a safety marker transmits, to a command and control device that intervenes in a feedback loop controlling shot parameters: the cavitation doses $MDD_a$ delivered in the fourth step, said doses varying during the shot; and/or the states Al1(a), Al2(a) of the first warning parameter and/or of the second warning parameter as determined in the fifth step.

Another subject of the invention is a system for performing spectral analysis and determining a safety marker that is representative of a state of destabilization of microbubbles contained in a region of a biological tissue, said bubbles being subjected to an ultrasonic excitation signal emitted at a predetermined emission frequency $f_0$ in order to induce localized and reversible opening of the biological barriers in said region of the tissue, and said state of destabilization of the microbubbles being detrimental to the biological tissue, said ultrasonic excitation signal being formed by an ultrasonic sequence composed of a predetermined integer number Nb, higher than or equal to 1, of wave trains, called "shots". The system for performing spectral analysis and determining a safety marker is characterized in that it is configured to, after each shot Bb is triggered, b being comprised between 1 and Nb:

regularly measure, during the shot Bb, at a series of times ta, the variation as a function of time in the spectral lines corresponding to the subharmonic and/or ultra-harmonic frequencies of a received acoustic-response signal of the microbubbles, the received response signal being detected by a passive cavitation detector having a predetermined detection passband, and determine, by quantifying it, the variation as a function of time, over the times ta of the time series, in a safety marker that is defined, at each time ta, by a number MDDa equal to the ratio of the sum of the areas of the spectral lines, measured at the time ta and corresponding to the subharmonic and/or ultra-harmonic frequencies of the received acoustic-response signal of the microbubbles, to the sum of the areas of the spectral lines, measured at the first time t1 and corresponding to the subharmonic and/or ultra-harmonic frequencies of the acoustic-response signal of the microbubbles.

According to particular embodiments, the system for performing spectral analysis and determining a safety marker comprises one or more of the following features:

at each time ta, the measurement of the spectral lines corresponding to the subharmonic and/or ultra-harmonic frequencies of the received acoustic-response signal of the microbubbles exploits the response signal received in an observation window wa that contains the time ta and that is included in the reception time interval corresponding to the shot in question;

the observation or analysis windows wa are adjacent or separate or partially overlap pairwise and slightly on their edges.

Another subject of the invention is a computer program or product comprising a set of instructions that are configured to implement the method for performing spectral analysis and determining a safety marker, defined above, when they are loaded into and executed by one or more computers implemented in the system for performing spectral analysis and determining a safety marker, defined above.

Another subject of the invention is a system for providing ultrasonic assistance to a therapeutic treatment targeting a region of a soft vascularized biological tissue containing microbubbles, comprising:

a device for exciting and emitting a therapeutic sequence of one or more excitation shots at a predetermined emission frequency $f_0$, said shots being focused on the region to be treated of the biological tissue, a passive cavitation sensor for detecting and measuring the response of the microbubbles contained in the region in response to the shots of the sequence, a system for performing spectral analysis and determining a safety marker that is representative of a state of destabilization of the microbubbles, as described above, a command and control device for controlling parameters of the one or more shots of the ultrasonic exciting device, the passive cavitation sensor, the system for performing spectral analysis and determining a safety marker, the command and control device and the ultrasonic exciting device being placed in series in a chain so as to form a safety feedback loop.

BRIEF DESCRIPTION OF THE DRAWINGS

The invention will be better understood on reading the following description of a number of embodiments, which

Figure 1:
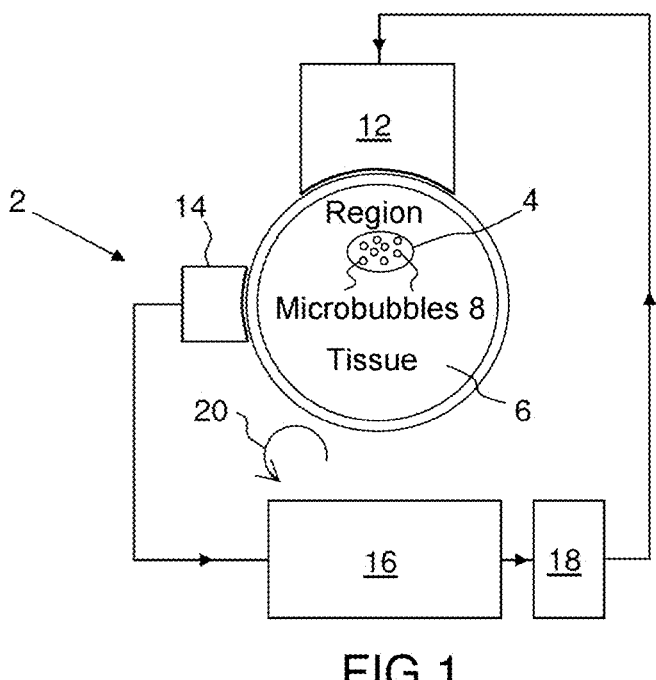
Figure 2:
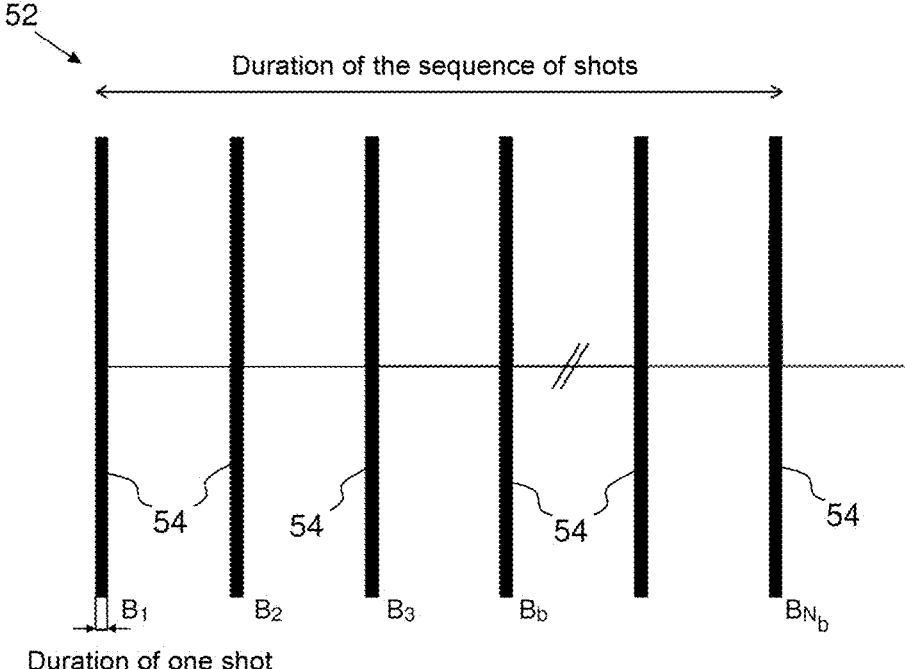
Figure 3:
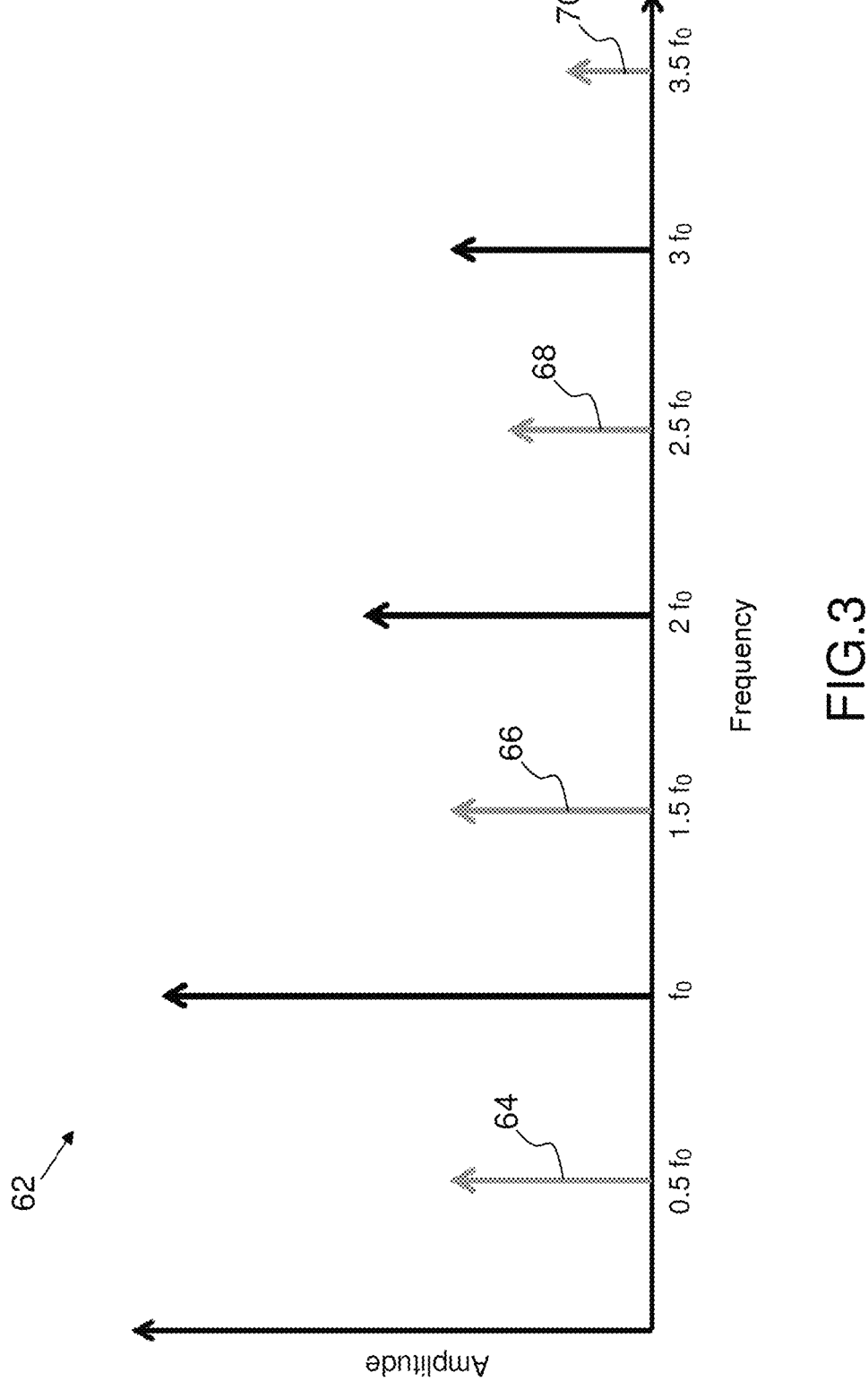
Figure 4:
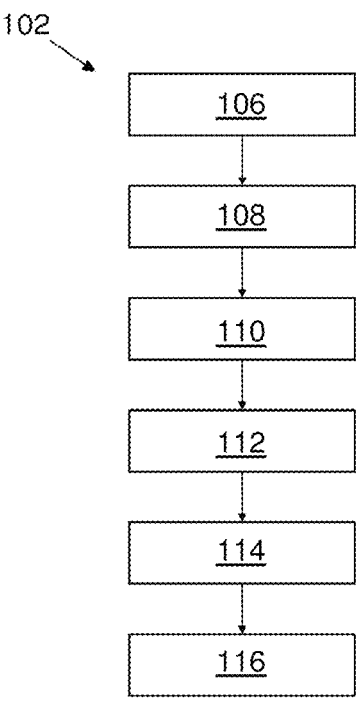
Figure 5:
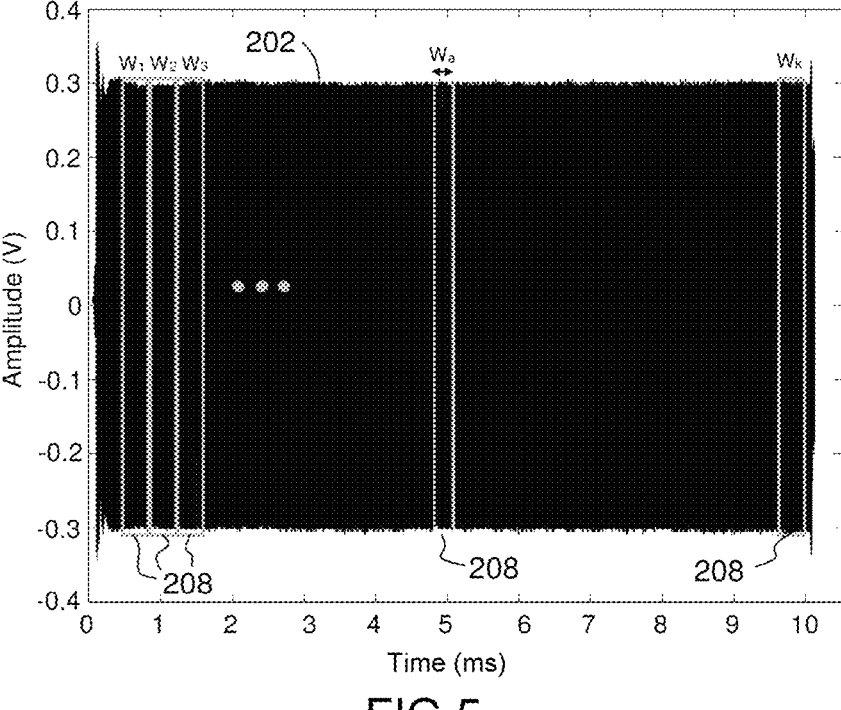
Figure 6:
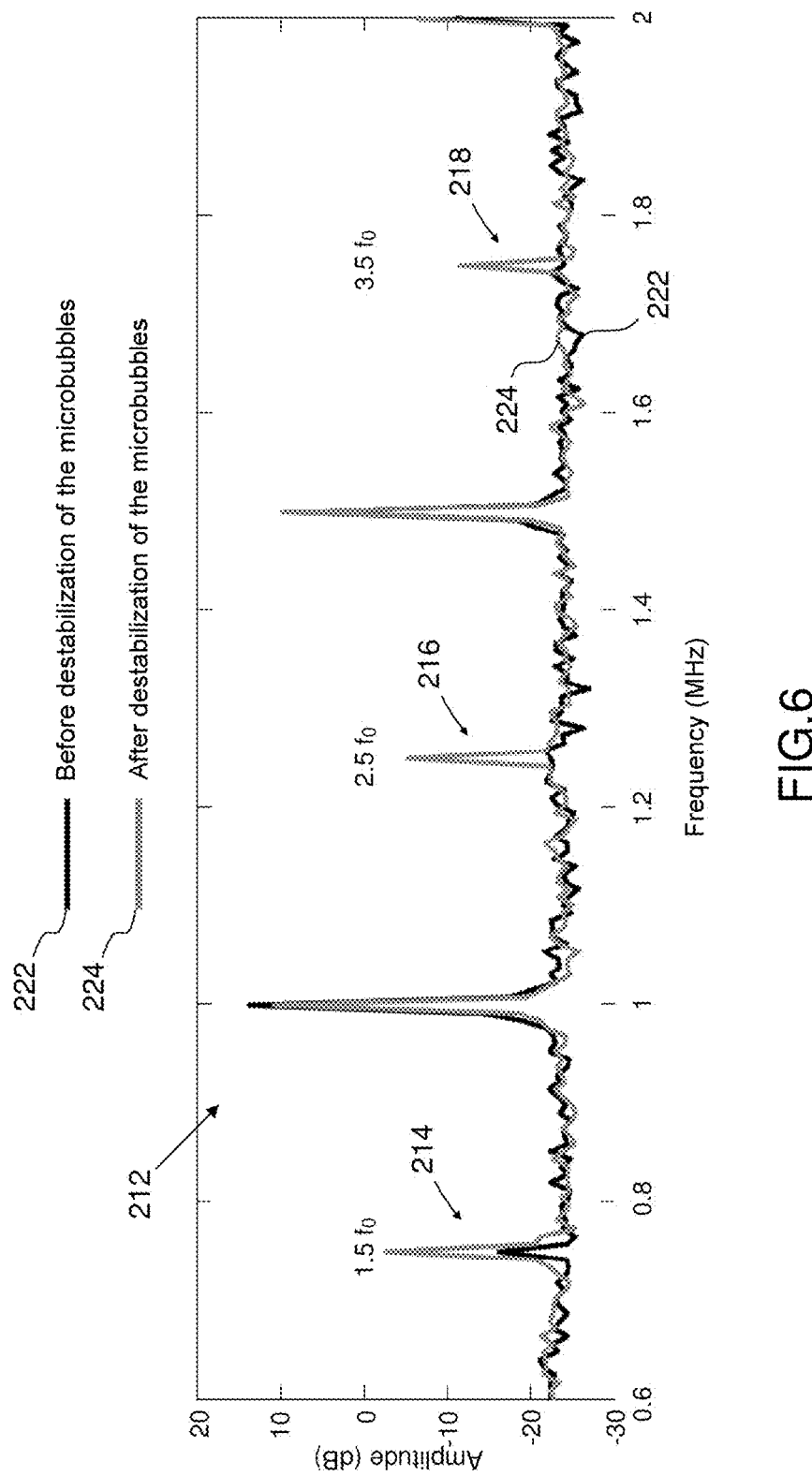
Figure 7:
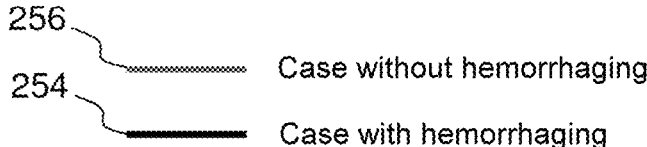
Figure 7:
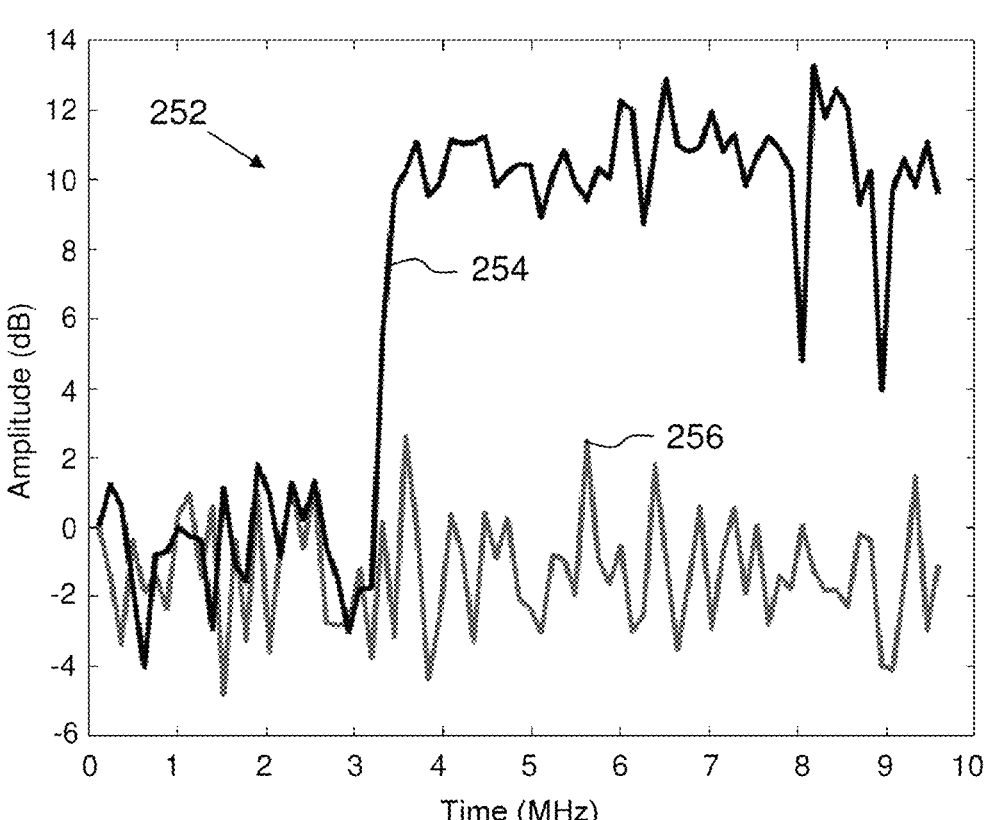
Figure 8A:
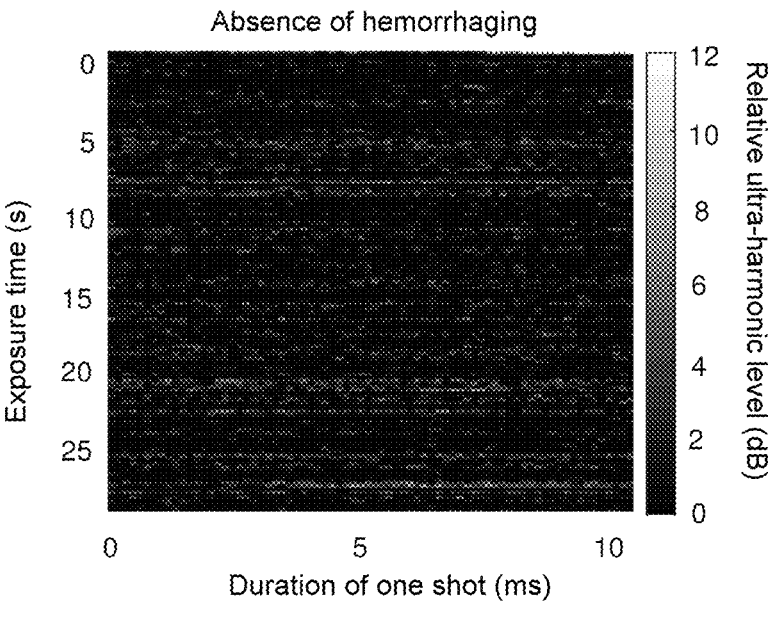
Figure 8B:
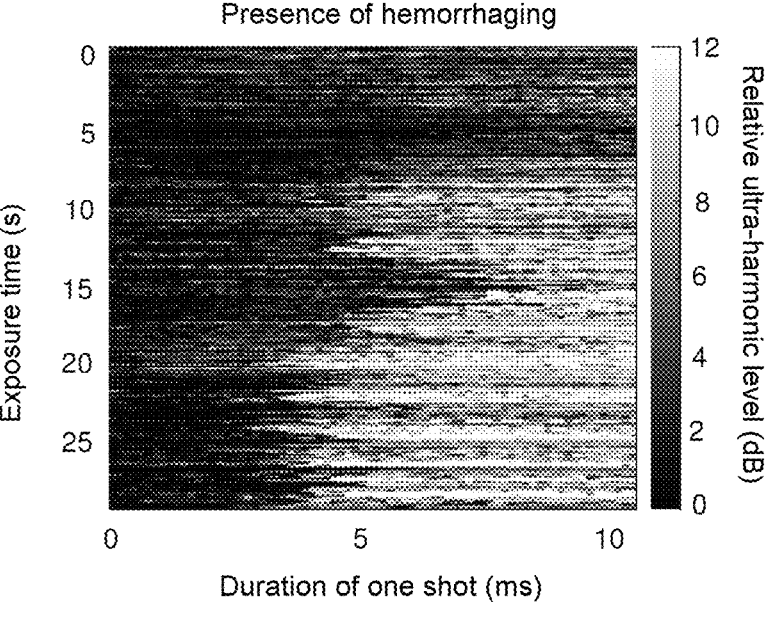

8 description is given solely by way of example and with reference to the drawings, in which:

FIG. 1 is a schematic view of a system for providing ultrasonic assistance to a therapeutic treatment targeting a region of a biological tissue containing microbubbles, a system for performing spectral analysis and determining a safety marker being integrated into said system for providing ultrasonic assistance;

FIG. 2 is a view of an ultrasonic sequence for therapy with gas microbubbles (e.g., opening of the blood-brain barrier, sono-permeabilization);

FIG. 3 is a view of the frequency content of the response of the microbubbles in response to the application of sequences of ultrasonic shots;

FIG. 4 is a view of the method for performing spectral analysis and determining a safety marker, said method being executed during each shot of a sequence;

FIG. 5 is a view of the break-up, into a plurality of time windows $w_a$, a varying from 1 to k, of the received cavitation signal originating from the microbubbles during one ultrasonic shot;

FIG. 6 is a view of an example of spectral responses before and after destabilization of the microbubbles during an ultrasonic excitation shot transmitted at 0.5 MHz into a primate brain;

FIG. 7 is a view of the variation in the dose of ultra-harmonic components ($1.5f_0$; $2.5f_0$; $3.5f_0$) obtained from the signal of the microbubbles (SonoVue) during a 10 ms shot at 500 kHz applied to a primate brain, a first example leading to the appearance of hemorrhaging and a second example not leading to hemorrhaging;

FIGS. 8A and 8B are views of measurements of the ultra-harmonic signal during ultrasonic sequences applied to a primate, in a non-hemorrhagic case (FIG. 8A) and a hemorrhagic case (FIG. 88).

DETAILED DESCRIPTION

In FIG. 1, a system 2 for providing ultrasonic assistance to a therapeutic treatment targeting a region 4 of a biological tissue 6 containing microbubbles 8 comprises:

a device 12 for exciting and emitting a therapeutic sequence of one or more excitation wave trains at a predetermined emission frequency $f_0$, said trains being called "shots" and being focused on the region 4 to be treated of the biological tissue 6;

a passive cavitation sensor 14, which is formed using one or more receiving transducers, for detecting and measuring the response of the microbubbles contained in the region 4 in response to the shots of the sequence;

a system 16 according to the invention for performing spectral analysis and determining a safety marker that is representative of a state of destabilization of the microbubbles 8; and a command and control device 18 for controlling parameters of the one or more shots of the exciting device 12.

The excitation frequency $f_0$ is chosen so as to allow a localized and reversible opening of the biological barriers to be induced in the treated region 4 of the tissue 8.

The passive cavitation sensor 14 has a reception passband that depends on the passband(s) of the receiving electroacoustic transducers.

The system 16 according to the invention for performing spectral analysis and determining a safety marker is made up, for example, of one or more electronic computers.

The system 16 according to the invention for performing spectral analysis and determining a safety marker is configured to, after each shot Bb of a sequence of a predetermined number Nb of shots has been triggered, Nb being an integer number higher than or equal to 1, and b, which is comprised between 1 and Nb, being an index indicating order in the sequence:

regularly measure, during the shot Bb, at a series of times ta, the variation as a function of time in the spectral lines corresponding to the subharmonic and ultra-harmonic frequencies of a received acoustic-response signal of the microbubbles, the received response signal being detected by a passive cavitation detector having a predetermined detection passband, and determine, by quantifying it, the variation as a function of time, over the times ta of the time series, in a safety marker that is defined, at each time ta, by a number $MDD_a$ equal to the ratio of the sum of the areas of the spectral lines, measured at the time ta and corresponding to the subharmonic and/or ultra-harmonic frequencies of the received acoustic-response signal of the microbubbles, to the sum of the areas of the spectral lines, measured at the first time t1 and corresponding to the subharmonic and/or ultra-harmonic frequencies of the acoustic-response signal of the microbubbles.

The command and control device 18 for controlling parameters of the one or more shots of the exciting device 12 is configured to receive information in real time from the safety marker and/or warning information, and, on the basis of this information, to inhibit the exciting device (stop the shot(s), modulate the parameters of the shot sequence) when the safety of the tissue requires it.

An automatic safety feedback loop 20 may be formed by placing in series, to form a chain, the cavitation sensor 14, the system for performing spectral analysis and determining a safety marker 16, the command and control device 18 for controlling parameters of the one or more shots, and the device 12 for exciting and emitting a therapeutic sequence of one or more ultrasonic shots, such as illustrated in FIG. 1.

An ultrasonic excitation signal is formed by an ultrasonic sequence composed of a predetermined integer number Nb, higher than or equal to 1, of wave trains, called "shots".

In FIG. 2, the therapeutic ultrasonic sequence 52 is composed of a plurality wave trains 54 (or "bursts"), which are referred to as "shots" below, and which are repeated, and separated by dwell times. Typically, shots of a duration comprised between 3 and 10 ms are repeated at a repetition frequency of value typically comprised between 5 and 10 Hz, for a sequence duration or exposure time of 30 seconds to 10 minutes.

As has already been described in the preamble, currently (stable or inertial) cavitation is detected by performing spectral analysis on the overall acoustic response of the microbubbles to a wave train, i.e. the average over the total duration of each shot. As mentioned above, the microbubbles may emit specific (sub-harmonic and ultra-harmonic) frequencies that are associated with their destabilization.

In FIG. 3, the appearance, in the total spectral content 62 of a shot, of lines at subharmonic and ultra-harmonic frequencies is illustrated. Here, one subharmonic line 64 is observed at $0.5f_0$ and three ultra-harmonic lines 66, 68, 70 are observed at $1.5 f_0$; $2.5 f_0$; and $3.5 f_0$, respectively. The appearance of subharmonic and ultra-harmonic lines is accentuated when shots of long duration, i.e. of a plurality of wave cycles at $f_0$, are transmitted.

In the invention, the cavitation signals are used and exploited to determine, in real time, a safety marker of the ultrasound therapy.

The invention is based on the measurement of the variation in the subharmonic and ultra-harmonic frequencies during an ultrasonic shot (an emitted excitation wave train) in order to ensure the safety of the therapeutic sequence. The data that led to the invention indicate that the appearance of lines at subharmonic and ultra-harmonic frequencies in the spectral content is a sudden effect that occurs during the ultrasonic shot and that then lasts for the duration thereof. Detection of this effect may be used immediately to stop the ultrasonic shot before resuming the next shot once new intact bubbles have entered into the shot volume. The sequence may also be adjusted dynamically in terms of ultrasonic amplitude and/or of the duration of the shots, in order to avoid repetition of the effect.

The idea of observing the appearance of this effect during the shot therefore allows the time from which said effect occurs to be precisely defined and thus the duration of the following shots of the ultrasonic sequence to be adjusted accordingly, i.e. either in a set manner, or preferably dynamically.

The measurement of this effect during the shot, according to the method of the invention, is more sensitive than conventional detection tools based on frequency analysis of a complete shot.

In the case of conventional analysis of the data measured by the cavitation sensor, these effects of sudden appearance may occur without being detected. Specifically, the conventional analysis amounts to taking an average of the frequency content over the complete shot. Obviously, should the effect appear at the end of the shot, this averaging will mask the subharmonic and ultra-harmonic components and hence they will not be observed (or not to the point they should be) during the frequency analysis.

In addition to this effect of dilution of the useful parameter by averaging, it should be noted that shot-by-shot tracking of this sort observes independent events given that each shot is fired at a different cloud of bubbles. The conventional strategies proposed up to now, which analyze the response signal to the complete shot, use as reference a signal acquired before injection of the microbubbles. This acquisition allows, inter alia, the signal reflected by the bone and the non-linear propagation of ultrasound in the medium to be taken into consideration. However, this acquisition is performed several seconds to several minutes before the treatment. This acquisition is constraining because it must be repeated for all the ultrasound amplitudes that will potentially be evaluated during the injection of the microbubbles and for all the positions of the transducer during the therapy. It requires the ultrasound system and the patient to remain perfectly immobile throughout the treatment.

In contrast, according to the invention, it is the variation in the signal of the same bubbles during the shot, i.e. the dynamics of their destabilization under ultrasound, that is observed by comparing the bubbles to themselves at the start of the shot. Since reference is made to the same bubbles a few cycles beforehand, with their recent exposure to ultrasound as the only variable, it makes sense that more physically relevant parameters will be returned by such an analysis. With the method of the invention, the aforementioned difficulties encountered with conventional strategies disappear, since the reference signal is measured in the first window w1 of the shot during the treatment and the application of the ultrasound. As a result thereof, time is saved and causes of distortion avoided.

Generally, a method for performing spectral analysis and determining a safety marker according to the invention is implemented by the system 16 for performing spectral analysis and determining a safety marker.

The safety marker according to the invention is representative of a state of destabilization of microbubbles contained in the region 4 of the biological tissue 6, said microbubbles 8 being subjected to the ultrasonic excitation signal at the predetermined emission frequency $f_0$ in order to induce localized and reversible opening of the biological barriers in said region 4, and said state of destabilization of the microbubbles 8 being detrimental to the biological tissue 6.

The ultrasonic excitation signal is formed by an ultrasonic sequence composed of a predetermined integer number Nb, higher than or equal to 1, of shots.

The method for performing spectral analysis and determining a safety marker is characterized in that, after each shot Bb has been triggered, b being comprised between 1 and Nb, the system for performing spectral analysis and determining a safety marker:

regularly measures, during the shot Bb, at a series of a predetermined integer number k of times ta, a varying from 1 to k, the variation as a function of time in the spectral lines corresponding to the subharmonic and ultra-harmonic frequencies of the received acoustic-response signal of the microbubbles, the received response signal being detected by a passive cavitation detector having a predetermined detection passband, and determines, by quantifying it, the variation as a function of time, over the times ta, in a safety marker that is defined, at each time ta, by a number MDDa equal to the ratio of the sum of the areas of the spectral lines, measured at the time ta and corresponding to the subharmonic and/or ultra-harmonic frequencies of the received acoustic-response signal of the microbubbles, to the sum of the areas of the spectral lines, measured at the first time t1 and corresponding to the subharmonic and/or ultra-harmonic frequencies of the acoustic-response signal of the microbubbles.

The measurement, at each time ta, of the spectral lines corresponding to the subharmonic and ultra-harmonic frequencies of the received acoustic-response signal of the microbubbles exploits the response signal received in an observation window wa that contains the time ta and that is included in the reception time interval corresponding to the shot in question.

The observation or analysis windows wa are adjacent or separate or partially overlap pairwise and slightly on their edges.

It should be noted that, on the one hand, the first window w1 which serves as reference may be slightly offset with respect to the start of the shot so as to give the signal time to stabilize, and that, on the other hand, the duration of the window w1 in which the reference spectrum is computed may be longer than the duration of a consecutive observation window or than the duration of the sum of a plurality of consecutive windows. This allows a less noisy reference spectrum to be obtained.

In FIG. 4, a method 102 for performing spectral analysis and determining a safety marker according to the invention, which method is executed during each shot Bb of a sequence, b being comprised between 1 and Nb, comprises a set of steps 106, 108, 110, 112, 114 and 116.

In a first measuring and segmenting step 106, the temporal-response signal of the microbubbles 8 to the ultrasonic shot Bb is broken up into a predetermined integer number k, k being higher than or equal to 2, of time windows wa, a varying from 1 to k, of equal durations that allow the variation in the frequency components during the ultrasonic wave train Bb to be determined, said signal having been received and detected beforehand by the passive cavitation detector 14.

The number k of windows wa and their sizes tw will depend directly on the length $T_B$ and on the frequency $f_0$ of the ultrasonic shot used for therapy.

Typically, in current work reversible opening of the barrier is obtained with ultrasonic shots the length of which varies from a few microseconds to several tens of milliseconds. From a theoretical point of view, two time windows of equivalent size suffice to implement the method. The first time window w1 is then used as reference, the second window w2 allowing the variation in the signal received from the microbubbles to be observed.

However, if the number k of windows is not high enough, it will be impossible to determine with precision (this precision being dependent on the number and size of the windows) the time of appearance of the subharmonic and ultra-harmonic frequencies, and therefore to effectively adjust the times and amplitude of the ultrasonic shots in the sequence. Be that as it may, use of time windows that are too long will result in averaging of the frequency content of the received signal, making it difficult to detect the sub-harmonic and ultra-harmonic frequencies. It is therefore recommendable to subdivide the collected signal into a multitude k of consecutive, relatively short (of a few tens of ultrasonic cycles if possible) time windows in order to increase the sensitivity of the method.

In a spectra-computing second step 108, which is executed after the first step 106, for each time window wa (a, 1<a<k), the frequency spectrum of the portion, of the acoustic-response signal of the microbubbles to the wave train Bb, that is contained in said window wa is computed in order to allow an analysis of the signal to be performed in the frequency domain.

Preferably, the method for computing the frequency spectra uses a Fourier transform.

The number of cycles $n_c$ in the time signal considered must be sufficiently high ($n_c > 8$ ultrasonic cycles) in order to avoid overlap of the frequency components during the spectral analysis.

In summary, and taking into account the requirements of the first step 106 and the second step 108, the duration of the windows wa is comprised between 8 cycles and half the duration $T_B$ of a shot. The number k of windows wa is higher than or equal to 2 and lower than or equal to one eighth of the product of the duration of one shot $T_B$ multiplied by the ultrasonic excitation frequency $f_0$.

In a third step 110 of computing the variation, during the shot Bd, in a cavitation signal s(a), which step is executed after the second step 108, for each time window wa, a varying from 1 to k, the cavitation signal s(a) is computed from the representation of the signal in the frequency domain, which representation is delivered in the second step 108, to be the sum of the areas of the spectral lines measured at the time ta and corresponding to the subharmonic and/or ultra-harmonic frequencies of the acoustic-response signal of the microbubbles.

The number of ultra-harmonic components to be considered may vary depending on the devices and the passband of the one or more transducers used for the cavitation detection. It is a question of the signal-to-noise ratio of the detection of the various components. The analysis may be carried out on one component (preferably $f_0/2$ or $3f_0/2$, which are the most intensely radiated by the bubbles) or a plurality of components ($f_0/2$, $3f_0/2$, $5f_0/2$, and $7f_0/2$, for example, or more if the passive cavitation sensor 14 allows it).

It should be noted that the amplitude of the peaks due to these ultra-harmonic and/or subharmonic components may also be considered in this computation of the cavitation signal, in addition to or instead of the area of the spectral lines under the curve of the spectral bands. The spectral bands $\Delta f$ used to compute these frequency components depend on the emission frequency $f_0$ and on the sampling frequency of the measuring device and on the duration of the time windows wa. The work carried out in respect of this invention has demonstrated that the method may be effectively applied for spectral bands $\Delta f$ ranging from $0.04*f_0$ to $0.5*f_0$ with a preference for about $0.1*f_0$. The width of the spectral band must be tailored to the number of cycles of the time window in order to minimize measurement noise. When the number of cycles no is high, the spectral band $\Delta f$ must be narrow, and, vice versa, when the number of cycles $n_c$ is low, the spectral band $\Delta f$ must be wide.

It should be noted that, as a variant, the cavitation signal may be computed separately for each of the ultra-harmonic and/or subharmonic components and, in an associated manner, a decision tree of more complex feedback strategies may be employed. For example, depending on the passband of the cavitation sensor and the ambient electronic noise (greater at low frequency), if the amplitude of the component at $f_0/2$ "explodes", i.e. becomes excessive, but the amplitude of the component at $3f_0/2$ remains acceptable, then in an attempt to apply feedback the amplitude of the beam is decreased without cutting it short, the shot finally being cut short if the amplitude of the component at $3f_0/2$ ends up "exploding" as well.

In a fourth step 112 of computing the variation, during the shot Bb, in a cavitation marker s(a), which step is executed after the third step 110, for each time window wa of the shot Bb, a varying from 1 to k, the system for performing spectral analysis and determining a safety marker computes a safety marker $MDD_a$ called the "cavitation dose $MDD_a$". MDD standing for Microbubble Destabilization Dose, this safety marker being defined by a number $MDD_a$ equal to the ratio of the cavitation signal s(a) in the a-th window wa to the cavitation signal s(1) of the first time window w1, i.e.

$$MDD_a = \frac{s(a)}{s(1)},$$

the cavitation dose MDDa being expressed on a linear or logarithmic scale.

Generally, the observation or analysis windows wa are adjacent or separate or partially overlap pairwise.

The execution of the first, second, third and fourth steps may be sequenced in a serial or pipeline mode.

For example, in a first embodiment, the analysis of the temporal-response signal is performed in successive adjacent time windows.

In a second embodiment, the analysis of the temporal-response signal is performed in sliding time windows, always with normalization with respect to the cavitation signal s(1) of the first window.

In a fifth step 114 of computing the variation, during the shot Bb, in a first warning parameter Al1 and/or in a second warning parameter Al2, which step is executed by the system for performing spectral analysis and determining a safety marker after the fourth step 112, the first warning parameter Al1 is put in an active state when the safety marker MDDa exceeds a first predetermined safety threshold value Th1, and the second warning parameter Al2 is put in an active state when the number of times nf of the safety marker MDDa has exceeded the first threshold value Th1 has exceeded a second predetermined threshold value Th2. This number of times nf may be counted either for consecutive shots or alternatively for shots that are not necessarily consecutive.

In a sixth step 116, which step is executed after the fourth step 112 or the fifth step 115, the system for performing spectral analysis and determining a safety marker transmits the following data to the command and control device that intervenes in a feedback loop controlling the shot parameters:

the cavitation doses $MDD_a$ delivered in the fourth step, said doses varying during the shot; and/or the states Al1(a), Al2(a) of the first warning parameter and/or of the second warning parameter as determined in the fifth step.

For example, if the cavitation dose $MDD_a$ exceeds a first safety threshold Th1, which may vary between 6 and 22 dB depending on the data and the post-processing thereof, a preferred value being about 8 dB, the ultrasonic sequence of shots may either be adjusted in real time via a feedback loop, the control parameters being comprised among a decrease of the acoustic pressure, a decrease of the duration of the shots, and optionally the spacing between the shots, or stopped to avoid any undesirable ultrasound-related effects. It is also possible to define, by way of second safety threshold Th2, a tolerable maximum number of (consecutive or non-consecutive) shots that may exceed the threshold MDD, i.e. the first safety threshold Th1.

To date, no method and system for providing ultrasonic assistance to a therapeutic treatment using the marker $MDD_a$ of the invention to ensure the safety of an ultrasonic therapeutic sequence has been made known to the public. Currently, the frequency analysis of the cavitation signal is carried out on the whole of the response signal emitted by the microbubbles in response to each shot.

The break-up of the signal received in response to a shot, into at least two time windows, allows the appearance of the lines corresponding to subharmonic and/or ultra-harmonic components to be observed during the shot. This appearance effect can neither be observed nor quantified correctly without breaking up the received cavitation signal up into at least two time windows.

Advantageously, the safety bio-marker $MDD_a$ according to the invention, its computing methods and its use to control, in the context of a feedback loop, the acoustic properties of the shot beam make it possible to avoid bubble destabilization, which is generated by the modification of the envelope of the bubble and by the diffusion of the gas initially contained therein, and which may lead to locally violent physical effects that may be the cause of detrimental biological effects.

Again advantageously, and although the main motivation behind the invention was to improve the safety of the treatment protocol, avoiding destabilization of the microbubbles allows them to be kept active in the blood flow longer, and thus the total time for which said microbubbles may be used to keep the blood-brain barrier (BBB) open to be increased, and thus the effectiveness of the treatment to be increased.

The use of the MDD safety marker according to the invention may allow the length of the shots to be increased, the amplitude of the beam to be increased or the duty cycle of the shots to be increased, provided that the established threshold of harm, a threshold of 8 dB for example, is not reached during any of said shots. By guaranteeing a lesser destabilization of the microbubbles, the time they spend circulating in the blood is increased and, therefore, the total possible time of interaction with the vessel walls is increased. The MDD safety marker according to the invention may therefore serve as an efficiency optimization tool, this tool possibly being combined with other more conventional tools such as harmonic cavitation dose.

In FIG. 5, an example of an acoustic-response signal 202 of a medium formed from microbubbles, bone tissue and soft tissue to a wave train, i.e. a shot, of 10 ms transmitted to a primate at a frequency $f_0$ of 0.5 MHz is shown. The response 202 of the microbubbles to the ultrasonic shot has been broken up into 75 equivalent time windows wa (reference number 208 in the figure), a varying from 1 to 75, of 128 µs duration.

It should be noted that the first window w1 does not necessarily start at the start time of the acquired response signal. Here in FIG. 5, a delay of 160 µs has been introduced. This allows the electronic measurement signal to stabilize and makes comparison with the other windows possible.

FIG. 6 shows an example of the variation 212 in the dose of the ultra-harmonic components 214, 216, 218 at the respective frequencies $1.5f_0$; $2.5f_0$; $3.5f_0$ between a first spectral response 222 (black line) before destabilization of the microbubbles and a second spectral response 224 (gray line) after destabilization of the microbubbles. The first and second spectral responses 222, 224 were measured in two consecutive observation time windows during a 10 msec shot at 500 kHz applied to a primate brain with a view to opening the blood-brain barrier, based on the microbubble response signal received by the passive cavitation sensor. The received response signal was measured with an acoustic transducer that formed the cavitation sensor and the reception passband of which was centered on 1.5 MHz.

The time interval separating the measurement of the first spectral response and the measurement of the second spectral response was equal to the duration of one observation time window, i.e. 128 µs.

The ultra-harmonic signal at the ultra-harmonic frequencies $1.5f_0$. $2.5f_0$. $3.5f_0$ corresponding to a destabilization of the microbubbles appears clearly in the second spectrum, compared to the first spectrum, with a clear increase in the associated cavitation signal s(a).

Thus, based on the spectral analysis carried out in each time window of the shot response signal, the destabilization of the microbubbles may be detected.

In FIG. 7, the variation 252 in the dose of ultra-harmonic components ($1.5f_0$; $2.5f_0$; $3.5f_0$) obtained from the signal of the microbubbles (SonoVue) during a 10 ms shot at 500 kHz applied to a primate brain is illustrated, a first example, which led to the appearance of hemorrhaging, being described by a first curve 254 (black line), and a second example, which did not lead to hemorrhaging, being described by a second curve 256 (gray line).

The first and second variation curves 254, 256 demonstrate that the appearance of the ultra-harmonic components is a sudden effect that occurs after a certain time depending on the applied ultrasonic parameters, on the patient and on the environment subjected to the ultrasound. Specifically, a long excitation causes repeated oscillation of the bubbles, leading to a potential destabilization thereof after a number of excitation cycles. Under the present ultrasonic conditions. i.e. wave trains of 10 ms at 500 kHz in primates and at 650 kHz in rats, the study results as regards the invention indicate that the average time of appearance of the effect is 5.4 msec in primate brains and 3.2 msec in rat brains. In practice, an MDD threshold of 8 dB has been used as a marker of a microbubble-destabilization event.

FIGS. 8A and 88 show examples of a case (FIG. 8A) where no detrimental effects were seen and of a case (FIG. 8B) where hemorrhaging was observed in a primate brain.

The destabilization of the microbubbles that is induced by the ultrasonic sequence is characterized by the appearance of ultra-harmonic frequencies (light color in FIG. 8B) during the ultrasonic shot. Observation of this specific effect is associated with observation of hemorrhaging in the primate, as confirmed by magnetic resonance imaging (MRI).

For these examples, over a period of ultrasonic excitation of 30 s, the frequency of appearance of the effect was 73.8% in the hemorrhagic case and 0.7% in the non-hemorrhagic case. The repeated appearance of this effect, i.e. more than two events in consecutive shots, is associated with the presence of undesirable effects (edemas and hemorrhaging) in animals.

It should be noted that this example was limited to the study of ultra-harmonic frequencies (first three ultra-harmonics) because the limited reception passband of the ultrasonic cavitation sensor did not allow a reliable measurement to be taken of the subharmonic component in this example. However, the use of a cavitation detection transducer suitable for measuring the subharmonic signal would allow a similar study to be carried out on the subharmonic component.

In FIG. 8B, it is possible to discern two different times: vertically, the number of shots before the bubbles start to emit ultra-harmonics during the shot. Then horizontally from this time, the time from the start of the shot before they start to emit said ultra-harmonics. These two times are important and provide information on the quality of the bubbles in the medium.

The invention claimed is:

1. A system for performing spectral analysis and determining a safety marker that is representative of a state of destabilization of microbubbles contained in a region of a soft vascularized biological tissue, said microbubbles comprising an envelope and said microbubbles having an initial state, said microbubbles being subjected to an ultrasonic excitation signal at a predetermined emission frequency $f_0$ in order to induce localized and reversible opening of one or more biological barriers in said region, and said state of destabilization of the microbubbles being a modification of said initial state of the microbubbles associated with a buckling of the envelope of the microbubbles and detrimental to the soft vascularized biological tissue, said ultrasonic excitation signal being formed by an ultrasonic sequence composed of a predetermined integer number Nb, higher than or equal to 1, of wave trains, called "shots"; and wherein the system is configured to, after each shot Bb is triggered, b being comprised between 1 and Nb:

regularly measure, during each said triggered shot Bb in a series of times ta, a variation as a function of time in one or more spectral lines corresponding to one or more subharmonic and/or ultra-harmonic frequencies of an acoustic-response signal received from the microbubbles, the acoustic-response signal being detected by a passive cavitation detector having a predetermined detection passband, and determine and quantify, the variation as a function of time, over the times ta of said series of times ta, in a safety marker that is defined, at each time ta of said series of times ta, by a number $MDD_a$ equal to a ratio of a sum of the areas of the spectral lines, measured at said time ta and corresponding to the one or more subharmonic and/or ultra-harmonic frequencies of the acoustic-response signal of the microbubbles, to the sum of the areas of the spectral lines, measured at a first time t1 of said series of times ta and corresponding to the one or more subharmonic and/or ultra-harmonic frequencies of the acoustic-response signal of the microbubbles in said initial state of the microbubbles, and wherein said spectral lines corresponding to the one or more subharmonic and/or ultra-harmonic frequencies of the acoustic-response signal of the microbubbles exploits the acoustic-response signal received in an observation window or analysis window (wa) that contains said time ta and that is included in a reception time interval corresponding to said triggered shot Bb, the system being configured, for one of the shots Bb called given shot Bb, in a first measuring and segmenting step, to break up the acoustic-response signal of the microbubbles to the given shot Bb into a predetermined integer number k, k being higher than or equal to 2, of time windows wa, a varying from 1 to k, of equal durations that allow a variation in frequency components during the given shot Bb to be determined, said acoustic-response signal being received and measured by the passive cavitation detector, the duration of the time windows wa being comprised between a duration of 8 cycles of the ultrasonic excitation signal and half a duration $T_B$ of one shot; and/or the number k of time windows wa being higher than or equal to 2 and lower than or equal to one eighth of the product of the duration TB of one shot multiplied by the predetermined emission frequency $f_0$.

2. The system of claim 1, wherein the observation or analysis windows (wa) are adjacent or separate or partially overlap pairwise.

3. The system of claim 1, wherein the number k of time windows wa and their sizes tw depend directly on a duration and on the predetermined emission frequency $f_0$ of the given shot Bb, the duration of the given shot being comprised between at least one microsecond and hundreds of milliseconds.

4. The system of claim 1, configured to, a shot Bb being given with b comprised between 1 and Nb, in a spectra-computing second step, which is executed after said first measuring and segmenting step, compute, for each of the time windows wa of the shot Bb, a varying from 1 to k, a frequency spectrum of a portion, of the acoustic-response signal of the microbubbles to the shot Bb, that is contained in said window wa.

5. The system of claim 4, wherein the spectra-computing of the frequency spectrum uses a Fourier transform.

6. The system of claim 4, configured to, in a third step of computing a variation, during the shot, in a cavitation signal s(a), which step is executed after the spectra-computing second step, compute, for each time window wa, a varying from 1 to k, the cavitation signal s(a) to be the sum of the areas of the spectral lines measured at the time ta and corresponding to the one or more subharmonic and/or ultra-harmonic frequencies of the acoustic-response signal of the microbubbles.

7. The system of claim 6, wherein a number of ultra-harmonic and/or subharmonic components considered in the computation of the cavitation signal s(a) depends on the predetermined detection passband of one or more transducers used to detect the cavitation and that form the passive cavitation detector.

8. The system of claim 6, wherein said one or more ultra-harmonic and/or subharmonic components corresponds to measured peaks in said spectral lines, and wherein an amplitude of the measured peaks of the one or more ultra-harmonic and/or subharmonic components comprised in the predetermined detection passband of the passive cavitation detector are used in addition to or instead of the cavitation signal s(a) in the third step of computing.

9. The system of claim 6, configured to, in a fourth step of computing a variation, during the shot, in said cavitation signal s(a), which step is executed after the third step, compute, for each time window wa of the shot Bb, a varying from 1 to k, a cavitation dose safety marker defined by the number MDDa equal to a ratio of the cavitation signal s(a) in the a-th window of time windows wa to a cavitation signal s(1) of a first time window w1, the cavitation dose being expressed on a linear or logarithmic scale.

10. The system of claim 9, configured to, for one of the shots Bb called given shot Bb, b being comprised between 1 and Nb, in a fifth step of computing a variation, during the shot, in a first warning parameter Al1(a) and/or in a second warning parameter Al2(a), which step is executed after the fourth step, put the first warning parameter Al1(a) in first active state when the cavitation dose safety marker exceeds a first predetermined safety threshold value Th1, and put the second warning parameter Al2(a) in a second active state when a number of times nf the cavitation dose safety marker has exceeded the first predetermined safety threshold value Th1 has exceeded a second predetermined threshold value Th2.

11. The system of claim 10, configured to, in a sixth step, which step is executed after the fifth step, transmit, to a controller device that intervenes in a feedback loop controlling shot parameters:

the cavitation dose delivered in the fourth step, said cavitation dose varying during the shot; and/or the variation of the first warning parameter Al1(a) and/or of the second warning parameter Al2(a) as determined in the fifth step.

12. A system for providing ultrasonic assistance to a therapeutic treatment targeting a region of a soft vascularized biological tissue containing microbubbles, said microbubbles, said microbubbles comprising an envelope and said microbubbles having an initial state, the system comprising:

an ultrasonic device configured for exciting and emitting an ultrasonic sequence of one or more excitation shots at a predetermined emission frequency $f_0$, said excitation shots being focused on the region to be treated of the soft vascularized biological tissue, a passive cavitation sensor for detecting and measuring a response of the microbubbles contained in the region in response to the excitation shots of the therapeutic sequence, a system for performing spectral analysis and determining a safety marker that is representative of a state of destabilization of the microbubbles, said state of destabilization of the microbubbles being a modification of said initial state of the microbubbles associated with a buckling of the envelope of the microbubbles, and a controller device for controlling parameters of the one or more excitation shots of the ultrasonic device, the passive cavitation sensor, the system for performing spectral analysis and determining a safety marker, the controller device and the ultrasound device being placed in series in a chain so as to form a safety feedback loop, wherein the safety marker is representative of the state of destabilization of microbubbles contained in the region of the soft vascularized biological tissue, said microbubbles being subjected to an ultrasonic excitation signal at the predetermined emission frequency $f_0$ in order to induce localized and reversible opening of one or more biological barriers in said region, and said state of destabilization of the microbubbles being detrimental to the soft vascularized biological tissue, said ultrasonic excitation signal being formed by the ultrasonic sequence composed of a predetermined integer number Nb, higher than or equal to 1, of wave trains, called "shots"; and wherein the system for performing spectral analysis and determining a safety marker is configured to, after each shot Bb is triggered, b being comprised between 1 and Nb:

regularly measure, during each of said triggered shot Bb in a series of times ta, a variation as a function of time in one or more spectral lines corresponding to one or more subharmonic and/or ultra-harmonic frequencies of an acoustic-response signal received from the microbubbles, the acoustic response signal being detected by a passive cavitation detector having a predetermined detection passband, and determine and quantify, the variation as a function of time, over the times ta of said series of times ta, in a cavitation dose safety marker that is defined, at each time ta of said series of times ta, by a number MDDa equal to a ratio of a sum of the areas of the spectral lines, measured at said time ta and corresponding to the one or more subharmonic and/or ultra-harmonic frequencies of the acoustic-response signal of the microbubbles, to the sum of the areas of the spectral lines, measured at a first time t1 of said series of times ta and corresponding to the one or more subharmonic and/or ultra-harmonic frequencies of the acoustic-response signal of the microbubbles in said initial state of the microbubbles, and wherein said spectral lines corresponding to the one or more subharmonic and/or ultra-harmonic frequencies of the acoustic-response signal of the microbubbles exploits the acoustic-response signal received in an observation window or analysis window (wa) that contains said time ta and that is included in a reception time interval corresponding to said triggered shot Bb, the system for performing spectral analysis and determining a safety marker being configured, for one of the shots Bb called given shot Bb, in a first measuring and segmenting step, to break up the acoustic-response signal of the microbubbles to the given shot Bb into a predetermined integer number k, k being higher than or equal to 2, of time windows wa, a varying from 1 to k, of equal durations that allow a variation in frequency components during the given shot Bb to be determined, said acoustic-response signal being received and measured by the passive cavitation detector, the duration of the time windows wa being comprised between a duration of 8 cycles of the ultrasonic excitation signal and half a duration $T_B$ of one shot; and/or the number k of time windows wa being higher than or equal to 2 and lower than or equal to one eighth of the product of the duration $T_B$ of one shot multiplied by the predetermined emission frequency $f_0$.

* * * * *